(12) United States Patent
Garrett

(10) Patent No.: US 6,243,604 B1
(45) Date of Patent: Jun. 5, 2001

(54) APPARATUS FOR CHARGING DEFIBRILLATOR CAPACITORS

(75) Inventor: Michael C. Garrett, Skokie, IL (US)

(73) Assignee: Medical Research Laboratories, Inc., Buffalo Grove, IL (US)

( * ) Notice: Subject to any disclaimer, the term of this patent is extended or adjusted under 35 U.S.C. 154(b) by 0 days.

(21) Appl. No.: 09/259,113

(22) Filed: Feb. 26, 1999

(51) Int. Cl.[7] .................................................. A61N 1/39
(52) U.S. Cl. ............................................. 607/5; 607/7
(58) Field of Search .................................... 607/5, 7

(56) References Cited

U.S. PATENT DOCUMENTS

| | | |
|---|---|---|
| 3,599,017 | 8/1971 | Oakes . |
| 3,659,178 | 4/1972 | Gilbert et al. . |
| 3,821,635 | 6/1974 | Kimmel et al. . |
| 3,886,932 | 6/1975 | Suessmilch . |
| 4,047,096 | 9/1977 | Madewell . |
| 5,426,561 | 6/1995 | Yen et al. . |
| 5,447,522 | 9/1995 | Chang et al. ............................. 607/7 |
| 5,470,343 | 11/1995 | Fincke et al. . |
| 5,483,165 | 1/1996 | Cameron et al. . |
| 5,484,452 | 1/1996 | Persson . |
| 5,700,280 | * 12/1997 | Silvian ..................................... 607/5 |
| 5,773,961 | 6/1998 | Cameron et al. . |
| 5,800,461 | 9/1998 | Menken et al. .......................... 607/7 |
| 5,959,371 | * 9/1999 | Dooley et al. ....................... 307/130 |

* cited by examiner

Primary Examiner—Carl H. Layno
(74) Attorney, Agent, or Firm—Fitch, Even, Tabin & Flannery

(57) ABSTRACT

Defibrillator capacitors are charged according to duty cycle control implemented by several stages of clocking circuits. A first frequency clocking circuit is reset on demand to introduce additional clock pulses for a fast charge of the capacitors.

19 Claims, 5 Drawing Sheets

APPARATUS FOR CHARGING DEFIBRILLATOR CAPACITORS

BACKGROUND OF THE INVENTION

1. Field of the Invention

The present invention pertains to the charging of capacitors used with defibrillators, and in particular external defibrillators.

2. Description of the Related Art

Cardiotherapeutic defibrillators, once used only by trained medical personnel, are now being made available for use by the general population, including individuals having little or no training. The defibrillators contemplated for general use are of the automatic external type and include on-board real time diagnostic capability to intervene or otherwise control the defibrillator therapy being administered. In general, the defibrillators deliver a relatively high voltage, low energy pulse or series of pulses to a patient suffering cardiac arrhythmias, such as ventricular fibrillation. The power supply relied upon to deliver the defibrillation therapy typically comprises one or more batteries carried on board the defibrillator unit or an electrical power utility supplying mains power to a building, for example.

Because of the nature of the electrical therapy required, it is not possible in a practical device to supply the therapeutic energy upon instantaneous demand, by drawing from the power source. Instead, energy from the power source must be accumulated over a certain period of time in one or more defibrillator capacitors which are later discharged to deliver the desired defibrillation therapy. It is particularly critical that the defibrillation therapy be delivered as quickly as possible, given the nature of the medical threat encountered. Accordingly, rapid charging of the defibrillator storage capacitor is required and advances in reducing charge time are still being sought.

Due to the nature of the use to which the defibrillation equipment is put, certain components employed must be carefully constructed to close performance tolerances which are expected to be closely maintained throughout the life of the component. It is important that such components are not unexpectedly stressed during unusual operating conditions, as when main power supply voltage unexpectedly drops. Also, it would be advantageous if a closer control could be exercised over the stress to which the electrical components are put.

SUMMARY OF THE INVENTION

It is an object of the present invention to provide a charging circuit for defibrillator capacitors.

It is another object of the present invention to provide a charging circuit which employs computer or other electronic control of the circuits operation, and in particular which allows direct control of peak current in the charging circuit.

A further object of the present invention is to provide a charging circuit for defibrillator capacitors in which a larger number of defibrillator therapy events can be generated despite a greater variation in source power conditions.

These and other objects of the present invention are provided in Apparatus for charging defibrillator capacitors, comprising:

a transformer having a primary winding with primary connection means for connection to a power supply, to draw current therefrom and a secondary winding with secondary connection means for connection to said defibrillator capacitors to supply charging power thereto, said pulse transformer having a magnetic field which rises and collapses while charging said defibrillator capacitors;

field monitoring means for detecting the collapse of magnetic field of said transformer and for sending a trigger signal in response thereto;

transformer control means coupled to said transformer primary winding to control current flow therethrough in response to a control signal;

a downstream pulse generator having an output coupled to said transformer control means to provide the control signal therefor, said downstream pulse generator also having an input for receiving a driving signal and a reset port for receiving a reset signal to reset said first pulse generator, said downstream pulse generator producing an output signal pulse of pulse width determined in response to said driving signal and resettable in response to the reset signal received at said reset port;

a comparator having two inputs and an output which is coupled to said downstream pulse generator reset port;

a reference signal means coupled to one of said comparator inputs;

primary signal means coupled to the other of said comparator inputs, and producing a primary sensor signal in response to current flow through the transformer primary winding;

a multivibrator delivering a series of pulses, comprising said driving signal, to an output coupled to said downstream pulse generator input, said multivibrator further having a reset port for receiving a multivibrator reset signal so as to reset the series of pulses in response thereto;

an upstream pulse generator having an output coupled to said multivibrator reset port, an input for receiving an upstream input signal and an upstream pulse generator reset port for receiving a reset signal to reset said upstream pulse generator, said upstream pulse generator producing the multivibrator reset signal, comprising a series of reset pulses, in response to said upstream input signal;

said upstream pulse generator input coupled to said field monitoring means for receiving the trigger signal therefrom and for resetting the series of reset pulses in response thereto, thereby synchronizing the downstream pulse generator and hence said transformer control means to said collapse of magnetic field of said transformer.

DETAILED DESCRIPTION OF THE PREFERRED EMBODIMENTS

Turning now to FIG. 1, defibrillator apparatus includes a circuit for charging defibrillator capacitors is generally indicated at 10. As indicated in the inset in FIG. 1, the schematic diagram is read left to right across four FIGS. 1a–1d. Briefly, the circuit operates to charge a bank 12 of defibrillator capacitors 14 shown in the upper right corner of FIG. 1d. Referring to FIG. 1a, a FAST CHARGE DISABLE TERMINAL 20 is coupled to a computer 25 or other control device which lifts a disable command signal indicating that a fast charge is required. In the preferred embodiment, program control is implemented by a digital computer, although it will become readily apparent to those skilled in the art that conventional analog circuitry or an application specific integrated circuit (ASIC) could be employed in place of the computer.

Terminal 22 is connected to the same computer 25 and receives an instruction indicating that the CHARGE DISABLE signal is to be lifted in preparation for a therapeutic event. Terminal 24 is also connected to the same computer 25 to issue a pulse signal indicating a pulse width voltage command to be described herein. Terminal 26 located at the bottom of FIG. 1a indicates to the computer 25 that an overvoltage condition has been sensed in conventional overvoltage protection device 30, shown at the bottom of FIG. 1b.

Figure 1A:
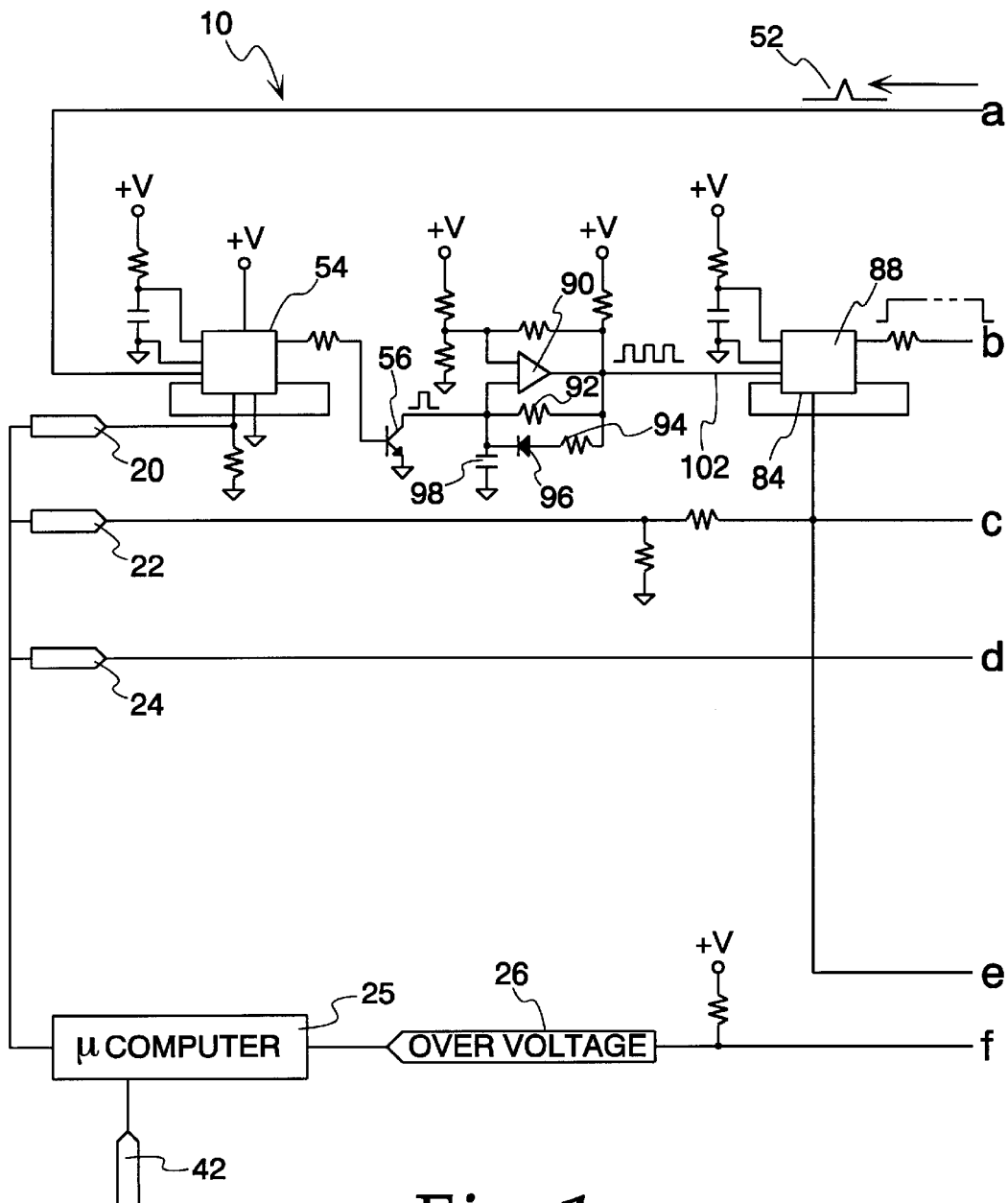
FIGS. 1a, 1b, 1c and 1d is a schematic diagram of a charging circuit according to the principles of the present invention.
Figure 1B:
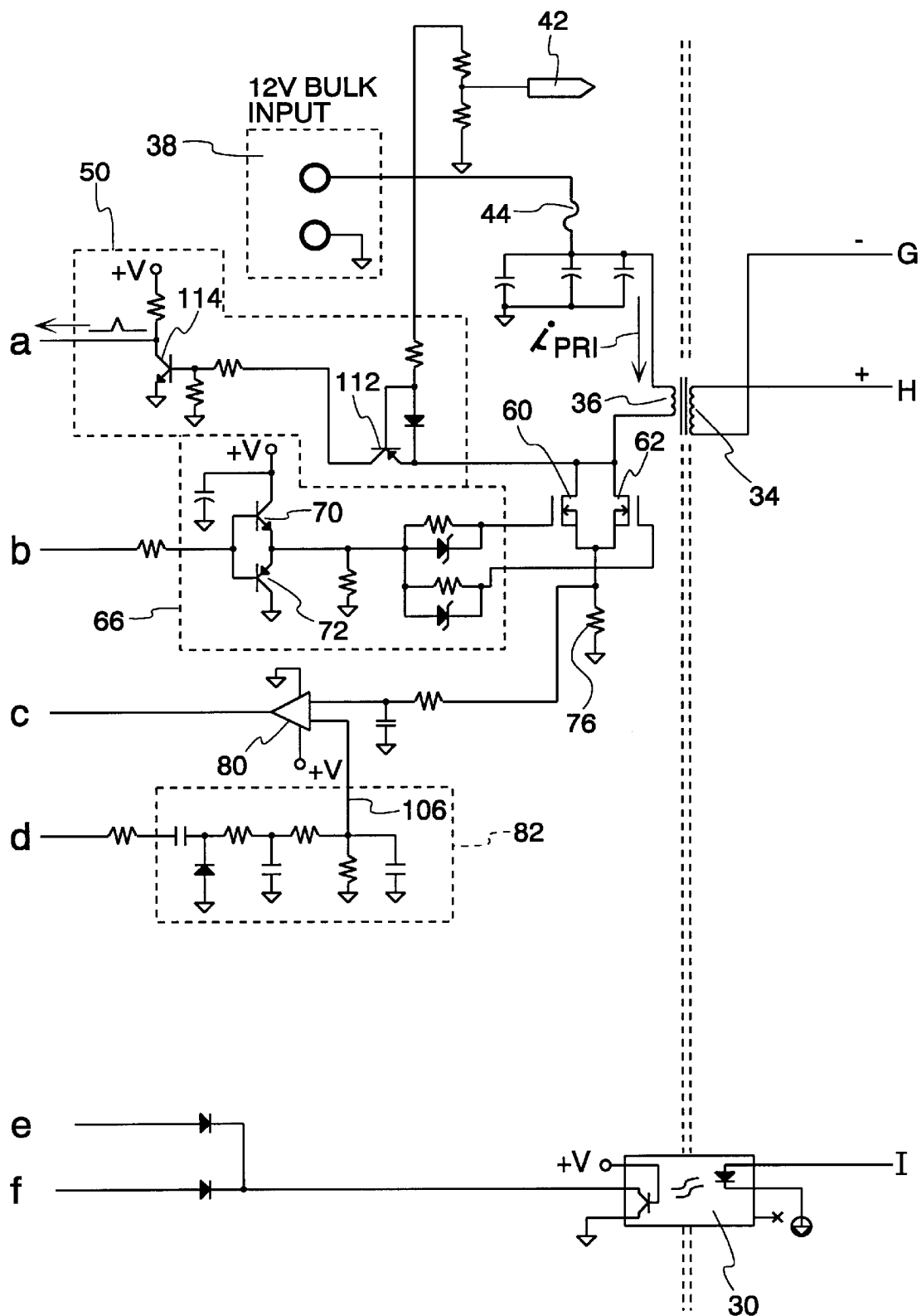

Turning to FIG. 1b, two sources of charging voltage are applied to the capacitor bank 12. One source, identified by reference numeral 125, charges the capacitor bank to an approximate twelve volt level. Power from a battery or other charger source 38 is delivered by the secondary windings of a pulse transformer 34. The primary windings 36 of the transformer 34 receive power from the energy source 38 which, for a portable external defibrillator of the preferred embodiment is delivered by a conventional 12 volt bulk input storage battery. As shown at the top of FIG. 1b, a voltage signal proportional to the battery voltage is sent to the computer 25 through a terminal 42. The voltage present at terminal 42 is also sent to computer 25.

The computer 25 responds to the battery voltage at terminal 42 to regulate further charging activity if the computer, based upon recent stored data of voltage-time characteristics of the battery indicate that the battery is about to enter a cut-off condition. If desired, the computer 25 commands can be overridden so as to deliver any remaining energy in the battery, even though a battery cut-off condition is imminent. Power to the transformer primary is carried through a conventional protective fuse 44. As indicated in FIG. 1b, a current $i_{PRI}$ flows through fuse 44 and constitutes the primary current in transformer 34. As will be seen herein, the primary current is computer controlled and the function of the reference voltage developed by the circuit 82.

Referring again to FIG. 1b, a field sensor circuit 50 shown at the top of FIG. 1b senses magnetic field collapse in transformer 34 and responds by delivering a trigger pulse 52 shown in symbolic form in the upper right-hand corner of FIG. 1a. The trigger pulse is delivered to an input of a monostable pulse generator 54. A FAST CHARGE signal is also applied by the computer 25 to a second input of monostable pulse generator 54. Output from the monostable pulse generator 54 is sent to switching transistor 56, altering the operation of circuitry controlling solid state switching devices 60, 62 shown in FIG. 1b. When switching elements 60, 62 are closed, the current path through the transformer primary is completed and current $i_{PRI}$ is drawn from the bulk power supply to charge the magnetic field in transformer 34.

Referring again to FIG. 1b, driver circuitry 66, including switching transistors 70, 72, provides the driving signals to high power switching devices 60, 62 causing those devices to conduct the primary transformer current $i_{PRI}$. As the primary current ramps up, a voltage develops across current sensing resistor 76 which in turn is fed to one input of comparator 80. The energy sensing element inputted to comparator 80 could also comprise a current sensing transformer, or a Hall effect device, if desired. As will be seen herein, the other input of comparator 80 receives a computer-controllable reference voltage from circuitry 82. When the transformer current-induced voltage across resistor 76 exceeds the reference voltage supplied to comparator 80, comparator 80 sends a reset signal to a reset input 84 of a monostable pulse generator 88, shutting off switch transistors 70, 72, and in turn the solid state power control devices 60, 62, thus terminating the current flow from the power supply flowing through the transformer primary 36.

Consideration will now be given to the interaction of the three stages which control drive circuitry 66 and in turn the current flowing through the transformer primary. The third stage, comprising monostable pulse generator 88, issues a series of pulses to driver circuit 66. Each pulse has a pulse width adjusted to limit primary current "on" time in transformer 34. Monostable pulse generator 88 is triggered on the rising edges of incoming pulses and tends to produce a corresponding number of fixed width pulses. However, the output pulses from the monostable pulse generator are automatically controlled by the present invention in that the pulse width duration is cut short by a selective, voltage control RESET. The current control to the transformer is implemented by comparator 80 which operates to cut off, i.e., reset monostable pulse generator 88 as required to limit the "switch on" time allowed, thereby limiting the peak current in the transformer primary circuit.

Preferably, the monostable pulse generator 88 is of the triggerable type and responds to a pulse rate at its input which is made variable according to other aspects of the present invention. As can be seen in FIG. 1a, conductor 102 transmits a pulse train to an input of monostable pulse generator 88. Conductor 102 receives the pulse train from the output of astable multivibrator 90. The inherent frequency of the astable multivibrator current is set to a value substantially lower than that needed for an optimal charging rate. Preferably, the frequency of the a stable multivibrator 90 is chosen at a "fail safe" level (e.g., on the order of 10 kHz) to assure that, in a free-running condition (herein termed the "slow charge" rate) the fly-back transformer 34 will not become saturated in otherwise uncontrolled, reasonably anticipated operation. As a frame of reference, the "slow charge" rate requires several minutes to fully charge a capacitor bank which has been pre-charged to an approximate 12 volt level. In order to selectively obtain greater performance from the charging circuit, the pulse rate of the pulse train on conductor 102 is selectively increased to frequencies approaching 60–70 Hz according to a number of predetermined FAST CHARGE circuit controls.

Referring again to FIG. 1a, the first stage controlling operation of driver circuit 66 includes monostable pulse generator 54. As mentioned, the input of this pulse generator is triggered by trigger pulses 52 received from field collapse detector circuit 50. When a FAST RATE DISABLE signal is lifted from terminal 20, the monostable pulse generator 54 is allowed to operate, generating a pulse with each field collapse within the fly-back transformer. Thus, the triggering of pulse generator 54 is synchronized to the collapse of field within the fly-back transformer, allowing the capacitor bank to be charged as quickly as possible while avoiding saturation of the transformer core. The output of monostable pulse generator 54 is coupled through a buffer stage, including transistor 56, to a reset input of the astable multivibrator 90. This causes the astable multivibrator reset to its output pulse train, in effect introducing an "augmentation" or forced pulse to occur ahead of the next regular (i.e., circuit-determined) pulse. This in turn causes the third stage, monostable pulse generator 88, to trigger at a time earlier than it would have been triggered by a free-running second stage (i.e., operation of multivibrator 90 in a free-running mode).

The enhanced, forced triggering of monostable pulse generator 88 is, as mentioned, needed in order to attain maximum charge rate for the capacitor bank. As mentioned, without the forced triggering of monostable pulse generator 88 (with resulting added augmentation pulses) a full charge on the capacitor bank will require at least several minutes of circuit operating time. With the forced triggering afforded by the first stage (that including monostable pulse generator 54), the same full charge condition is determined in approximately five seconds. As will be appreciated, there is an unlimited number of charge rates available between a forced maximum charge rate and a lower free-running charge rate.

Consideration will now be given to the operation of comparator 80 and its associated circuitry, including voltage reference circuit 82 and a primary current detection circuit comprising resistor 76. The reference voltage developed by circuitry 82, which responds to signals from terminal 24, is connected to the computer 25. The computer input signals preferably comprise a fixed frequency, variable pulse width pulse train. The output of circuitry 82 is coupled to one input of comparator 80, via conductor 106. The output voltage is proportional to the width of pulses inputted to the circuitry 82. The computer 25 adjusts the width of pulses in a constant frequency pulse train, causing the reference voltage on conductor 106 to vary accordingly. Thus, by altering the width of computer pulses present on terminal 24, the voltage at which the power switching elements 60, 62 are shut off can be directly controlled by the computer, and the voltage control can be implemented with a small number of relatively inexpensive components. When comparator 80 responds by generating an output signal, the monostable pulse generator 88 is shut off, shutting off the drive transistors 70, 72 which in turn opens the power control element 60, 62 thus interrupting flow of primary transformer current from the bulk supply 38. The present invention provides control of the peak and average power demands on the bulk power supply with relatively simple circuitry 82. If desired, circuitry 82 can be replaced with a monolithic digital to analog converter or, if desired, a simple voltage source can be used in place of the circuitry 82.

Referring again to sensing circuitry 50 which detects magnetic field collapse in transformer 34, transistors 112, 114 form a voltage sensor which senses the voltage across the primary 36 of transformer 34. A pulse is outputted from the collector of transistor 114 when the voltage across the transformer primary 36 drops back to or below the supply voltage of bulk supply 38. This pulse 52 synchronizes the three pulse defining stages which activate the driver stage. More significantly, the pulse 52 serves as a timing pulse inputted to monostable pulse generator 54 causing a retrigger of the astable multivibrator 90, producing a pulse through monostable pulse generator 88 to turn on driver stage transistors 70, 72 and hence power control elements 60, 62, starting another charging cycle.

Figure 1C:
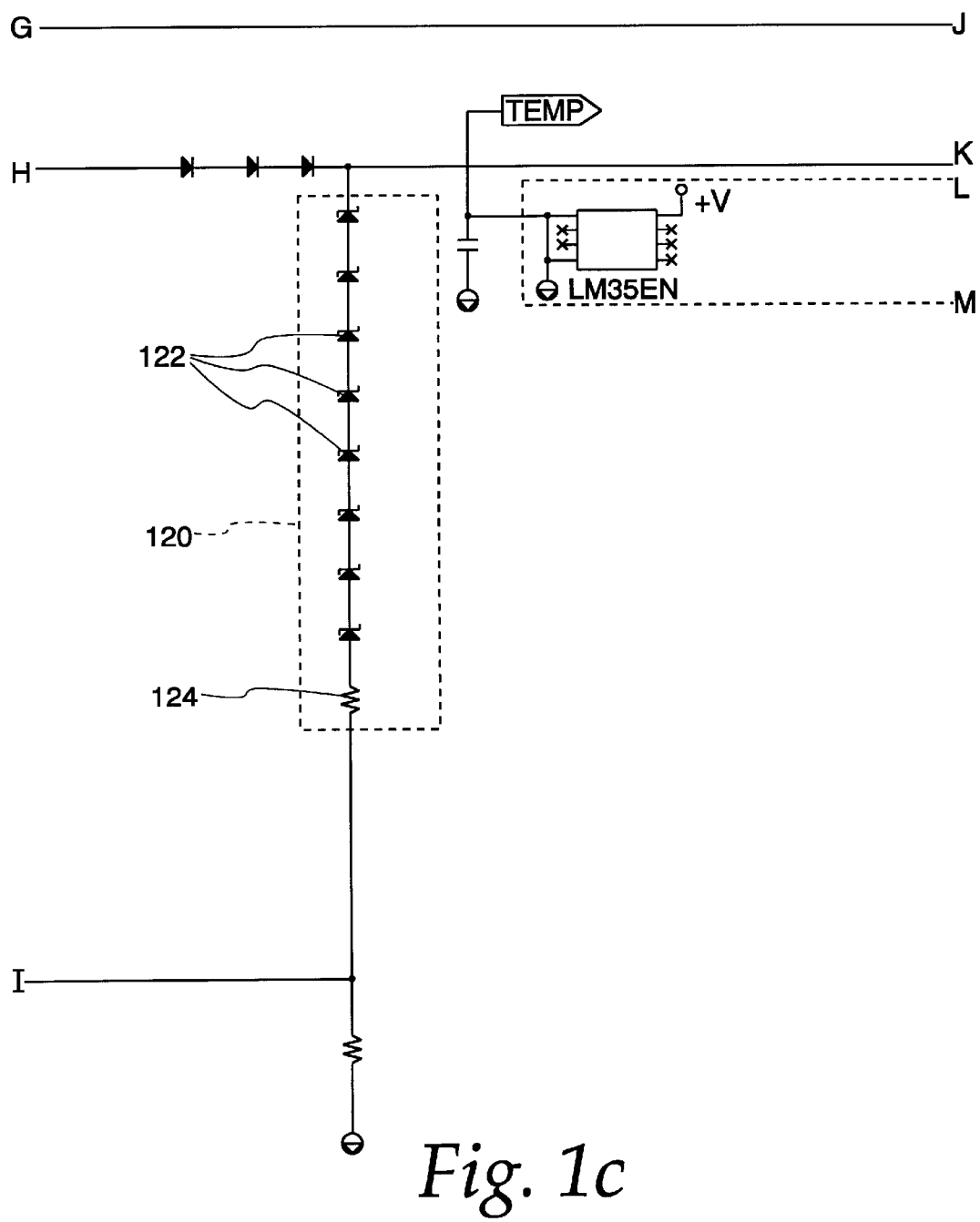
Figure 1D:
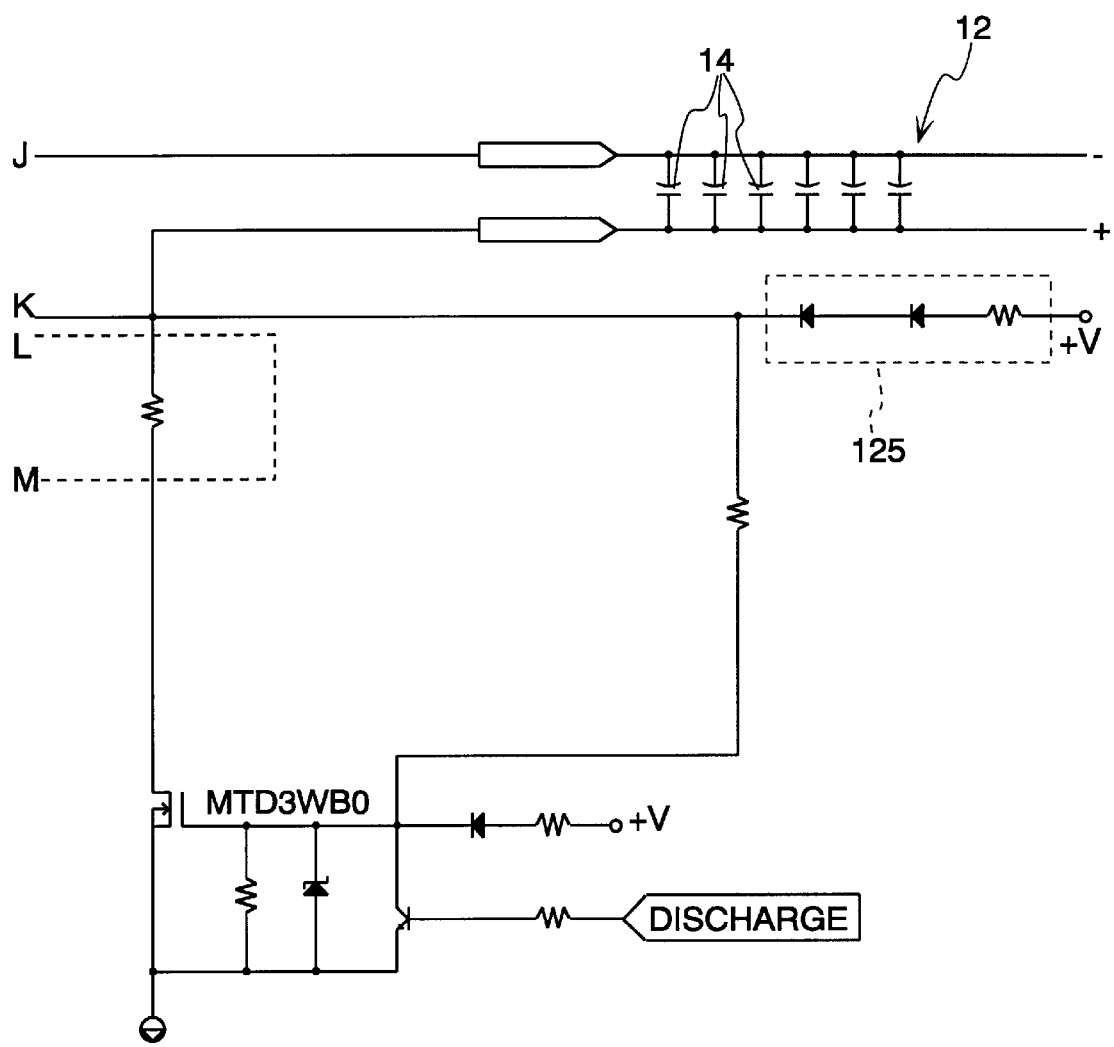

Referring to FIG. 1c, circuitry 120 includes zener diodes 122 and a resistor 124 which provides an overvoltage control triggering sensor 30 to inform computer 25, and send a shut down signal to port 84. Circuitry 120 allows the secondary current in the transformer 34 to decay at a practical, manageable rate when the primary current is cut off, thus permitting only a relatively small direct current in the primary winding 36 when a capacitor charging is initiated.

As mentioned, the primary current through winding 36 of transformer 34 flows through resistor 76, thus setting one voltage input of comparator 80 proportional to the energy stored in the fly-back transformer. The other input of comparator 80 is set by circuitry 82 under direct control from the computer 25. As a result, the primary current in transformer 34 is compared to a reference value that, when reached, terminates the switch drive pulse flowing through control elements 60, 62. This control operation wastes very little power when the current is being reduced due to a falling bulk supply voltage. If desired, the energy signal to the comparator can from the sensor of the magnetic field of the transformer (e.g., by use of a Hall effect sensor) or from a sensor of fields about a primary current conductor (e.g., by use of a current transformer).

As will now be appreciated, the capacitor charging circuit provides two closed loops for current control. An inside loop, including comparator 80, regulates current through the transformer primary in accordance with the pulse train outlet to terminal 24 by the computer 25. The outside loop feeds back battery voltage to terminal 42 of computer 25 preventing battery cut-off by regulating the average current flow out of the battery as a function of battery voltage. The computer 25 constantly monitors battery voltage and battery current drain and when battery cut-off conditions are predicted, program control within the computer 25 adjusts the pulse train at terminal 24, forcing the comparator 80 and associated circuitry downstream of comparator 80 to reduce current flowing through control elements 60, 62, thereby reducing the average current flow through the primary winding of the fly-back transformer.

As an interim control step, it is preferred that the computer attempt to provide maximum current flow to the transformer primary while sensing the battery voltage for a battery cut-off precursor condition. If the battery voltage drops to an unacceptable precursor level determined by a pre-set operating point, the computer will reduce the number of pulses in the pulse train entering terminal 24, or will transfer control to the free-running low frequency SLOW CHARGE mode of operation. As can be seen from the above, two modes of operation, one "fast charge" and the other "slow charge" are readily implemented with a minimum number of inexpensive components. Regardless of the mode of operation, the control circuit according to principles of the present invention provides an improved current mode control of both the peak and the average currents through the fly-back transformer primary, in turn controlling the saturation of the transformer core.

Figure 2:
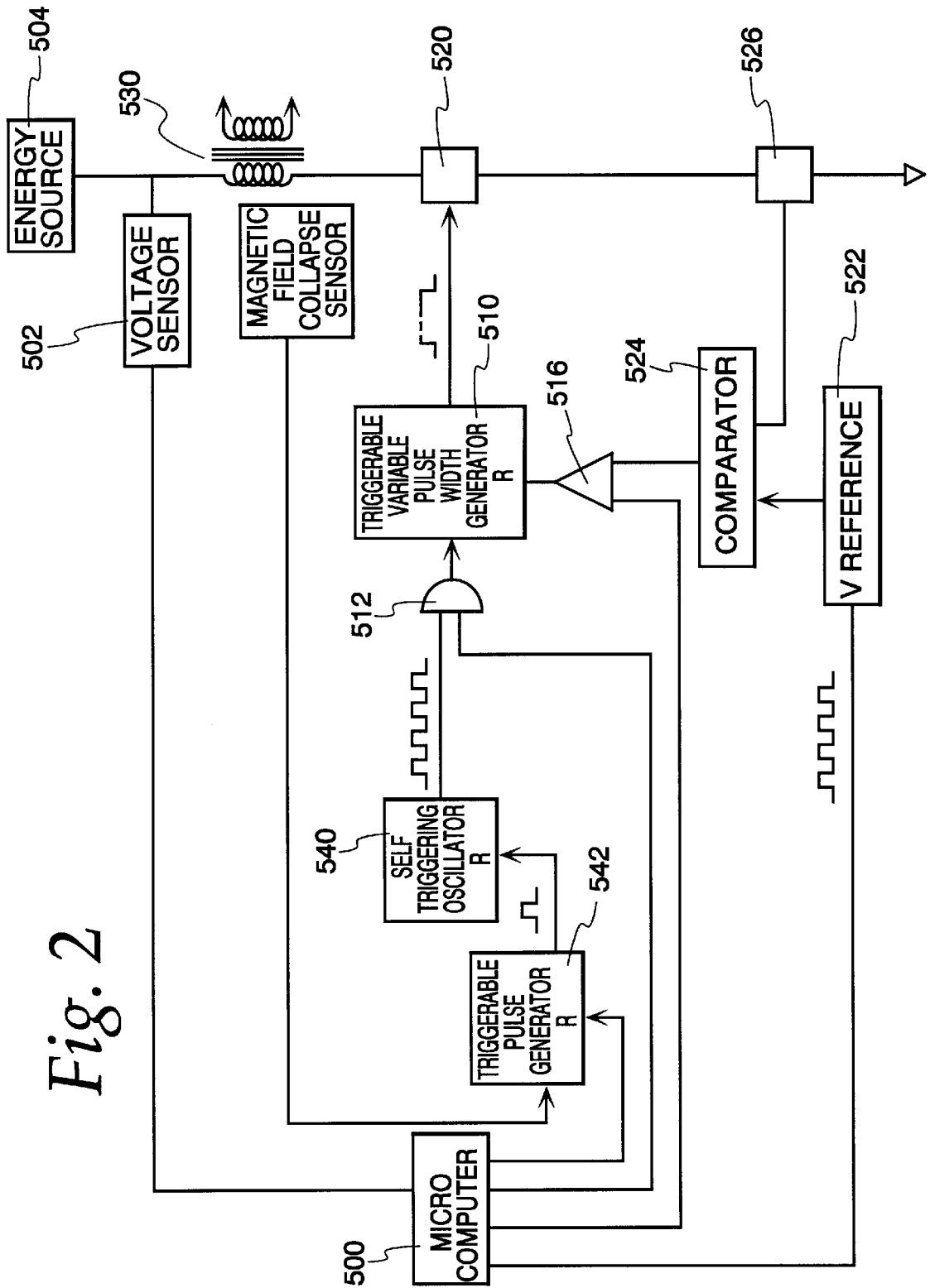
FIG. 2 is a schematic block diagram thereof.

Turning now to FIG. 2, a simplified block diagram of the circuit of FIG. 1 is shown. A microcomputer 500, analog operational amplifier or other control device receives data from voltage sensor 502, monitoring conditions of a battery or other energy source 504 for possible cut-off. The microcomputer controls input to a third stage 510, a variable pulse width generator, preferably one which is triggered by a pulse train. The third stage 510 switches transformer energy switch 520, controlling energy consumption of source 504. The microcomputer switches the incoming pulse train on and off by circuit function represented by an AND gate 512. This control lifts the energy demand on source 504.

As an alternative control, the microcomputer can directly control operation of the third stage 510 by setting the third stage by circuit function represented by an OR gate 516. The microcomputer could, for example, send continuous RESET commands to the third stage 510, or could "flash" the third stage at spaced apart intervals. The microcomputer has further control over the third stage by applying an input to reference stage 522, altering the reference level outputted by the stage 522. The inputs are preferably in the form of pulses, but could be a voltage ramp, frequency or current, for example. Stage 522 preferably operates on a voltage basis, but could operate on a current, frequency or other basis as well. The reference level is applied to a comparator 524 which receives a second input from an energy sensor 526 associated with the current, voltage, electric or magnetic fields of the energy source 504 and/or the fly-back transformer 530.

A synchronizing trigger pulse is generated by; the cycling of the fly-back transformer, and preferably by the collapse of its magnetic field. The synchronizing trigger pulse may be applied directly to the RESET point of a second stage 540, but preferably is buffered through a first stage 542 to provide a desired pulse definition in a stage made switchable under control of the microcomputer 500. The first stage is preferably a triggerable pulse generator, such as a monostable pulse generator. Most preferably, the first stage output is in pulse form, but could be in voltage, circuit or frequency form, if desired. The second stage 540 comprises a reference timing source, such as a clock chip, but preferably comprises a self-triggering oscillator and most preferably comprises an astable multivibrator whose output is fed to AND gate 512. The second stage preferably operates in a pulse mode, but could operate in a current, voltage or frequency mode as well to provide a resettable clocking control of the third stage 510. The third stage 510 has an output (preferably a pulse output) duration controllable by comparator stage 524 to provide duty cycle control of the switching stage 520. The pulse duration of stage 88 in the absence of a current reset pulse can be controlled by the maximum time out of the monostable multivibrator 510 to provide a maximum peak current or fail safe so the unit will continue in the absence of a reset pulse from 524.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. Apparatus for charging defibrillator capacitors, comprising:
    a transformer having a primary winding with primary connection means for connection to a power supply, to draw current therefrom and a secondary winding with secondary connection means for connection to said defibrillator capacitors to supply charging power thereto, said pulse transformer having a magnetic field which rises and collapses while charging said defibrillator capacitors;
    field monitoring means for detecting the collapse of magnetic field of said transformer and for sending a trigger signal in response thereto;
    transformer control means coupled to said transformer primary winding to control current flow therethrough in response to a control signal;
    a downstream pulse generator having an output coupled to said transformer control means to provide the control signal therefor, said downstream pulse generator also having an input for receiving a driving signal and a reset port for receiving a reset signal to reset said downstream pulse generator, said downstream pulse generator producing an output signal pulse of pulse width determined in response to said driving signal and resettable in response to the reset signal received at said reset port;
    a comparator having two inputs and an output which is coupled to said downstream pulse generator reset port;
    a reference signal means coupled to one of said comparator inputs;
    primary signal means coupled to the other of said comparator inputs, and producing a primary sensor signal in response to current flow through the transformer primary winding;
    a multivibrator delivering a series of pulses, comprising said driving signal, to an output coupled to said downstream pulse generator input, said multivibrator further having a reset port for receiving a multivibrator reset signal so as to reset the series of pulses in response thereto;
    an upstream pulse generator having an output coupled to said multivibrator reset port, an input for receiving an upstream input signal and an upstream pulse generator reset port for receiving a reset signal to reset said upstream pulse generator, said upstream pulse generator producing the multivibrator reset signal, comprising a series of reset pulses, in response to said upstream input signal;
    said upstream pulse generator input coupled to said field monitoring means for receiving the trigger signal therefrom and for resetting the series of reset pulses in response thereto, thereby synchronizing the downstream pulse generator and hence said transformer control means to said collapse of magnetic field of said transformer.

2. The apparatus of claim 1 wherein said downstream pulse generator comprises a monostable pulse generator.

3. The apparatus of claim 1 wherein said upstream pulse generator comprises a monostable pulse generator.

4. The apparatus of claim 1 wherein said multivibrator comprises an astable multivibrator.

5. The apparatus of claim 1 wherein said primary sensor signal comprises a voltage signal proportional to current flow through the transformer primary winding and said reference signal means comprises voltage reference means for generating a reference voltage signal.

6. The apparatus of claim 5 wherein said voltage reference means comprises a circuit for producing a voltage proportional to a number of pulses received.

7. The apparatus of claim 6 wherein said voltage reference means comprises a digital to analog conversion circuit.

8. The apparatus of claim 6 wherein said voltage reference means further comprises a fixed frequency, variable pulse width generator coupled to an input of said digital to analog conversion circuit.

9. The apparatus of claim 1 further comprising an overvoltage sensor having an output coupled to said downstream pulse generator reset port, said overvoltage sensor operatively associated with said transformer secondary winding to sense an overvoltage thereat, and to send a reset signal to said downstream pulse generator in response thereto.

10. The apparatus of claim 1 wherein the power supply comprises a storage battery, the apparatus further comprising means for monitoring the battery voltage during charging and for sending a reset.

11. Apparatus for charging a defibrillator capacitor, comprising:
    a transformer having a primary winding with primary connection means for connection to a power supply and a secondary winding with secondary connection means for connection to said defibrillator capacitor to supply charging power thereto, said pulse transformer having a magnetic field which rises and collapses while charging said defibrillator capacitor;
    transformer control means coupled to said transformer primary winding to control current flow therethrough in response to a control signal;

downstream clock pulse means having an output coupled to said transformer control means to send a control signal of a clock pulse type to said transformer control means, said downstream clock pulse means resettable to terminate a clock pulse being sent to said transformer control means when a reset signal is received by said downstream clock pulse means;

upstream clock pulse means having an output coupled to said downstream clock pulse means to send a control signal of a fixed frequency clock pulse type to said downstream clock pulse means, said upstream clock pulse means including pulse advancing means for advancing the time of occurrence of a next clock pulse ahead of that set by said fixed frequency clock pulse;

a comparator having two inputs and an output which is coupled to said downstream clock pulse means so as to cause said downstream clock pulse means to reset thereby terminating a clock pulse being sent to said transformer control means;

a reference signal means coupled to one of said comparator inputs;

primary energy sensor means coupled to the other of said comparator inputs, and producing a primary energy sensor signal in response to energy flow through the transformer primary winding; and said pulse advancing means comprises a reset port associated with said upstream clock pulse means to reset the next fixed frequency clock pulse to occur immediately at the output of said upstream clock pulse means, temporarily increasing the clock pulse frequency.

12. The apparatus of claim 11 wherein said pulse advancing means further comprises a triggerable pulse generator having an output coupled to said upstream clock pulse means reset port.

13. The apparatus of claim 12 wherein said pulse advancing means further comprises a field monitoring means for detecting the collapse of magnetic field of said transformer and for sending a trigger signal in response thereto to said triggerable pulse generator to cause said triggerable pulse generator to send a pulse to said upstream clock pulse means reset port, thereby causing said upstream clock pulse means to reset, advancing the time of the next clock pulse.

14. The apparatus of claim 11 wherein said primary energy sensor means comprises an electrical resistor.

15. The apparatus of claim 11 wherein said primary energy sensor means comprises a Hall effect sensor.

16. The apparatus of claim 11 wherein said primary energy sensor means comprises a current transformer.

17. Apparatus for charging a defibrillator capacitor, comprising:

a transformer having a primary winding with primary connection means for connection to a power supply and a secondary winding with secondary connection means for connection to said defibrillator capacitor to supply charging power thereto, said pulse transformer having a magnetic field which rises and collapses while charging said defibrillator capacitor;

transformer control means coupled to said transformer primary winding to control current flow therethrough in response to a control signal;

downstream clock pulse means having an output coupled to said transformer control means to send a control signal of a clock pulse type to said transformer control means, said downstream clock pulse means resettable to terminate a clock pulse being sent to said transformer control means when a reset signal is received by said downstream clock pulse means;

upstream clock pulse means having an output coupled to said downstream clock pulse means to send a control signal of a fixed frequency clock pulse type to said downstream clock pulse means, said upstream clock pulse means including pulse advancing means for advancing the time of occurrence of a next clock pulse ahead of that set by said fixed frequency clock pulse;

a comparator having two inputs and an output which is coupled to said downstream clock pulse means so as to cause said downstream clock pulse means to reset thereby terminating a clock pulse being sent to said transformer control means;

a reference signal means coupled to one of said comparator inputs;

primary energy sensor means coupled to the other of said comparator inputs, and producing a primary energy sensor signal in response to energy flow through the transformer primary winding; and said voltage reference means comprising a digital to analog conversion circuit for producing a voltage proportional to a number of pulses received.

18. Apparatus for charging a defibrillator capacitor, comprising:

a transformer having a primary winding with primary connection means for connection to a power supply and a secondary winding with secondary connection means for connection to said defibrillator capacitor to supply charging power thereto, said pulse transformer having a magnetic field which rises and collapses while charging said defibrillator capacitor;

transformer control means coupled to said transformer primary winding to control current flow therethrough in response to a control signal;

downstream clock pulse means having an output coupled to said transformer control means to send a control signal of a clock pulse type to said transformer control means, said downstream clock pulse means resettable to terminate a clock pulse being sent to said transformer control means when a reset signal is received by said downstream clock pulse means;

upstream clock pulse means having an output coupled to said downstream clock pulse means to send a control signal of a fixed frequency clock pulse type to said downstream clock pulse means, said upstream clock pulse means including pulse advancing means for advancing the time of occurrence of a next clock pulse ahead of that set by said fixed frequency clock pulse;

a comparator having two inputs and an output which is coupled to said downstream clock pulse means so as to cause said downstream clock pulse means to reset thereby terminating a clock pulse being sent to said transformer control means;

a reference signal means coupled to one of said comparator inputs;

primary energy sensor means coupled to the other of said comparator inputs, and producing a primary energy sensor signal in response to energy flow through the transformer primary winding; and means for selectively defeating operation of said upstream clock pulse means so as to produce a slow charge operation of said charging apparatus.

19. The apparatus of claim 10 further comprising an overvoltage sensor having an output coupled to said downstream pulse generator reset port, said overvoltage sensor operatively associated with said transformer secondary winding to sense an overvoltage thereat, and to send a reset signal to said downstream pulse generator in response thereto.

* * * * *